United States Patent [19]
Zipes et al.

[11] Patent Number: 5,366,486
[45] Date of Patent: Nov. 22, 1994

[54] AUTOMATIC FIBRILLATION DETECTOR AND DEFIBRILLATOR APPARATUS AND METHOD

[75] Inventors: Doulgas P. Zipes, Carmel; David E. Adams, Indianapolis, both of Ind.

[73] Assignee: Indiana University Foundation, Bloomington, Ind.

[21] Appl. No.: 15,650

[22] Filed: Feb. 9, 1993

Related U.S. Application Data

[63] Continuation-in-part of Ser. No. 904,409, Jun. 25, 1992, abandoned.

[51] Int. Cl.$^5$ .................... A61N 1/39; A61B 5/046
[52] U.S. Cl. ........................... 607/5; 128/705
[58] Field of Search ............. 607/14, 2, 4, 5; 128/705, 702, 696, 708

[56] References Cited

U.S. PATENT DOCUMENTS

| | | | |
|---|---|---|---|
| 3,937,226 | 2/1976 | Funke | 128/419 |
| 4,088,140 | 5/1978 | Rockland | 128/419 |
| 4,354,497 | 10/1982 | Kahn | 128/419 |
| 4,384,585 | 5/1983 | Zipes | 128/419 |
| 4,535,776 | 8/1985 | Strandberg et al. | 128/419 PG |
| 4,554,922 | 11/1985 | Prystowsky | 128/419 |
| 4,790,317 | 12/1988 | Davies | 607/4 |
| 4,799,493 | 1/1989 | DuFault | 128/705 |
| 4,830,006 | 5/1989 | Haluska et al. | 607/14 |
| 5,002,052 | 3/1991 | Haluska | 128/419 |
| 5,107,850 | 4/1992 | Olive | 128/705 |
| 5,117,824 | 6/1992 | Keimel et al. | 128/419 D |
| 5,158,092 | 10/1992 | Glace | 128/705 |
| 5,193,535 | 3/1993 | Bardy et al. | 128/419 D |
| 5,282,837 | 2/1994 | Adams et al. | 607/5 |

FOREIGN PATENT DOCUMENTS 0202748 11/1986 European Pat. Off. .

OTHER PUBLICATIONS

Computer Discrimination of atrial Fibrillation . . . , Jaince Slocum et al, May 1988.
Diagnosis of Atrial Fibrillation Using Electrograms . . . , Janice Jenkins et al, May 1988.
Automatic Methods for Detection of Tachyarrhythmias . . . , Frank Pannizzo et al, JACC vol. II, Feb. 1988.
Measurement of Differences in Timing and Sequence Between Two Ventricular Electrodes . . . , A. D. Mercando et al, PACE, vol 9, Nov.–Dec. 1986, Part II.

*Primary Examiner*—William E. Kamm
*Assistant Examiner*—Kennedy J. Schaetzle
*Attorney, Agent, or Firm*—Baker & Daniels

[57] ABSTRACT

The present invention involves an apparatus and method for detecting and treating fibrillation in the heart. Electrodes sense electrical activity in two distinct locations of the heart. The electrocardiac activations are monitored and the interval between activations at the two locations is measured and checked for variation. Upon detection of significant variation in the length of the intervals, the fibrillation condition is determined and a defibrillator is activated, so that a defibrillating shock may be delivered to the heart. For atrial fibrillation, the first defibrillating shock is relatively low and is increased until the fibrillation is no longer detected.

50 Claims, 5 Drawing Sheets

AUTOMATIC FIBRILLATION DETECTOR AND DEFIBRILLATOR APPARATUS AND METHOD

CROSS-REFERENCE TO RELATED APPLICATIONS

The present application is a continuation-in-part of copending U.S. patent application Ser. No. 07/904,409, filed on Jun. 25, 1992, now abandoned.

BACKGROUND OF THE INVENTION

1. Field of the Invention

The present invention relates to medical devices dealing with cardiovascular ailments. More particularly, the field of the invention is that of fibrillation detectors and defibrillators.

2. Description of the Related Art

Implantable cardioverters, or defibrillators, are known which monitor electrical activity to determine the presence of tachycardia or fibrillation in the ventricles of the heart and to deliver an electrical therapy to terminate the tachycardia. These prior art devices monitor electrical activity in the heart from a single pair of electrodes. For example, U.S. Pat. No. 4,384,585 to Zipes, entitled SYNCHRONOUS INTRACARDIAC CARDIOVERTER, the disclosure of which is explicitly incorporated by referenced herein, discloses an implantable medical device which senses tachyarrhythmias and delivers cardioverting pulses. Ventricular fibrillation is conventionally determined by observing the time interval in which the electrocardiogram (ECG) signal is at a baseline the determination of which is based on a probability density function. Another conventional method involves observing a shortened cycle length that is less than a cut-off value. The probability density function is often insufficiently sensitive to detect ventricular arrhythmia, while the shortened cycle length often results in overlapping with other arrhythmias such as sinus tachycardia or atrial fibrillation with a rapid ventricular response.

A difficulty in detecting fibrillation based on cycle length is that the observed characteristic does not uniquely identify the underlying arrhythmia. One problem with fibrillation detectors is that incorrect therapy may be delivered to patients with ECG readings that mimic ventricular tachycardia or fibrillation on the basis of cycle lengths. Although the determination of the exact type of arrhythmia may be improved by improving the probability density function and/or the rate cut-off detection approaches, greater specificity is desired to minimize the chance of making a false determination.

SUMMARY OF THE INVENTION

The present invention is a device and method which determines the presence of fibrillation with greater specificity, and administer defibrillating shocks to the heart. The present invention may be employed to determine the presence of atrial or ventricular fibrillation based on the disorganization of electrical activity (heart activation or pulse) in the atria and ventricles. In this manner, fibrillation is automatically and uniquely recognized because it is the only arrhythmia having the characteristic that the time interval between activations from the left and right sides of the heart are completely irregular. Monitoring this characteristic of heart activation eliminates the possibility that any other tachyarrhythmias would be interpreted as fibrillation. The device may also deliver defibrillating shocks to the heart to restore normal sinus rhythm after any fibrillation is detected.

The device of the present invention more accurately recognizes the presence of fibrillation by employing two recording electrodes, either bipolar or unipolar, and comparing the electrical activity recorded by each electrode. In atrial activity at two anatomically distinct locations, for example, one in the right atrium and the other in the coronary sinus. During atrial fibrillation, the recordings from these two locations are unrelated, i.e., both the rhythm or repetitive nature of the ECG recordings, as well as the rate of each location, are different between the two locations. Thus, the time interval between the recordings from the right and left atria (the $\Delta$ or delta activation interval) is constantly varying. In all other atrial or ventricular arrhythmias, the two locations still have a repetitive, common time interval between them, and therefore what occurs at one location occurs at the other location after a constant interval, i.e., the delta activation interval is constant. The present invention checks the time interval between the two recording electrodes of the heart and determines if sufficient interval variations, i.e., variations of the delta activation intervals, are present to indicate fibrillation.

The recording electrodes are placed at two different locations on the heart, for example, the coronary sinus and the right atrium or two atrial epicardial sites, to determine atrial fibrillation, or two ventricular epicardial sites or two right ventricular endocardial sites (or variations thereof) to establish the presence of ventricular fibrillation. The recording electrodes are connected with an electronic device which determines the degree of synchronization, i.e., the constancy of the delta activation interval, of the respective electrograms from the two electrodes. The electronic device may be dedicated hardware or a general purpose processor with appropriate software which determines the existence of variations in the intervals indicating fibrillation and delivers an appropriate defibrillating shock or shocks.

The fibrillation detector of the present invention monitors the two different cardial sites and determines the delta activation interval between each cycle. The percent change in the delta activation intervals from one cycle to the next, i.e., the delta of the delta activation interval, is calculated and compared to a threshold percentage; and a sufficiently large change may indicate the occurrence of an event. The frequency of such events may then be compared to a threshold frequency to determine whether a fibrillation condition should be indicated. For example, a sample of N intervals may be used to determine fibrillation by storing N intervals in an array, so that each new interval detected is shifted into the array, then the number of events in the new array is again compared to the threshold frequency to determine if fibrillation exists.

The detector circuitry may include a microprocessor or an Application Specific Integrated Circuit (ASIC). The fibrillation detector of the present invention may be combined with a defibrillator and with other sensor or control circuitry. For example, a blood pressure detector, temperature sensor, $CO_2$ monitor, etc. may be used in conjunction with the fibrillation detector of the present invention. This would allow a defibrillation controller to evaluate multiple aspects of the heart's condition previous to deciding on whether to administer defibrillating shocks.

The device of the present invention delivers the defibrillating shock in a careful and controlled manner. First, a low level shock is delivered and the heart monitored for the continued existence of fibrillation. If fibrillation is still present, the device delivers a second shock at a slightly higher level and again checks for fibrillation. This is repeated until the defibrillating shocks are successful. The defibrillating shock can be delivered to the atria, ventricles, or the entire heart.

BRIEF DESCRIPTION OF THE DRAWINGS

The above mentioned and other features and objects of this invention, and the manner of attaining them, will become more apparent and the invention itself will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplifications are not to be construed as limiting the scope of the invention in any manner.

DESCRIPTION OF THE PREFERRED EMBODIMENT

Figure 1:
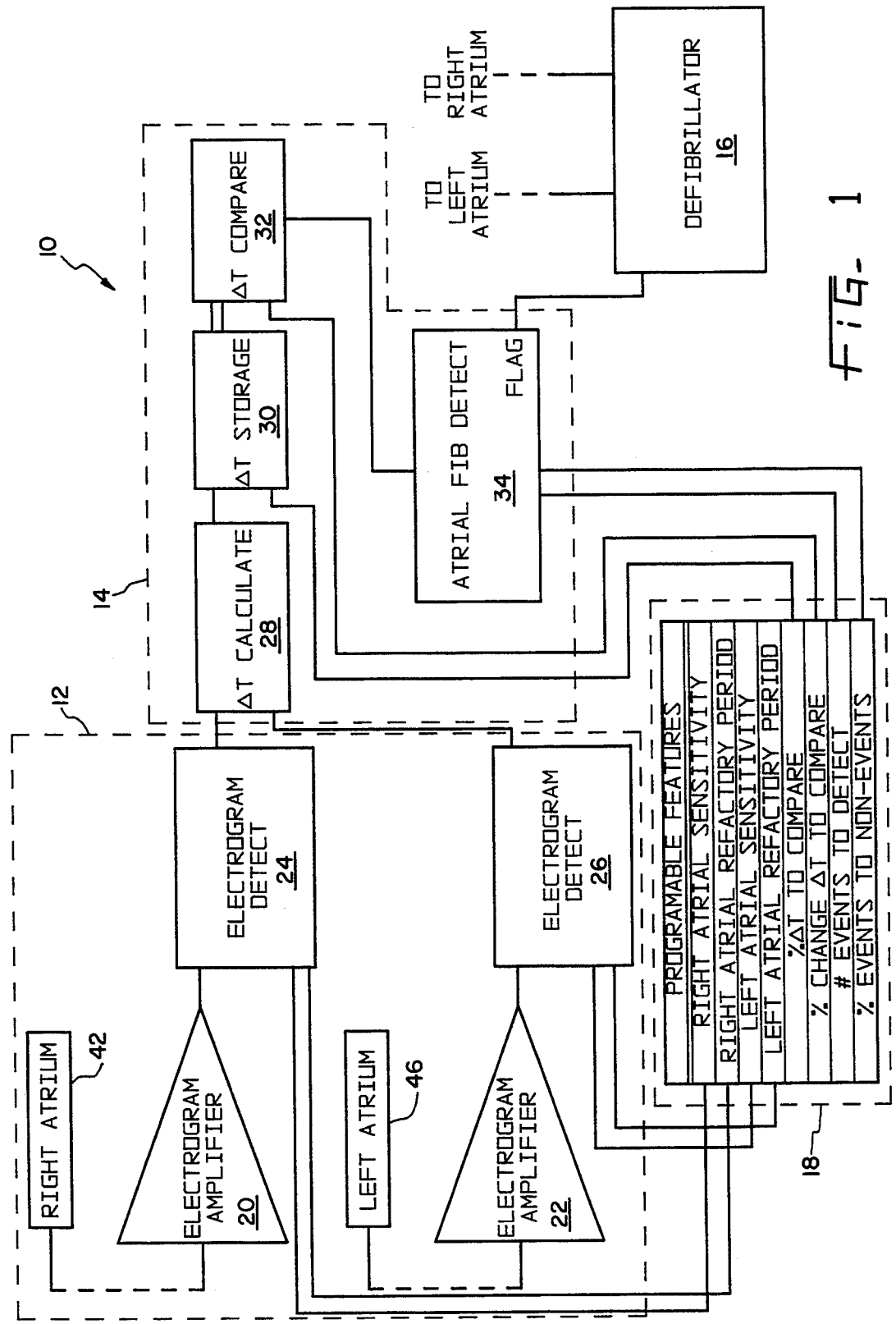
FIG. 1 is a schematic diagram of the fibrillation detection and defibrillation device of the present invention.
Figure 3:
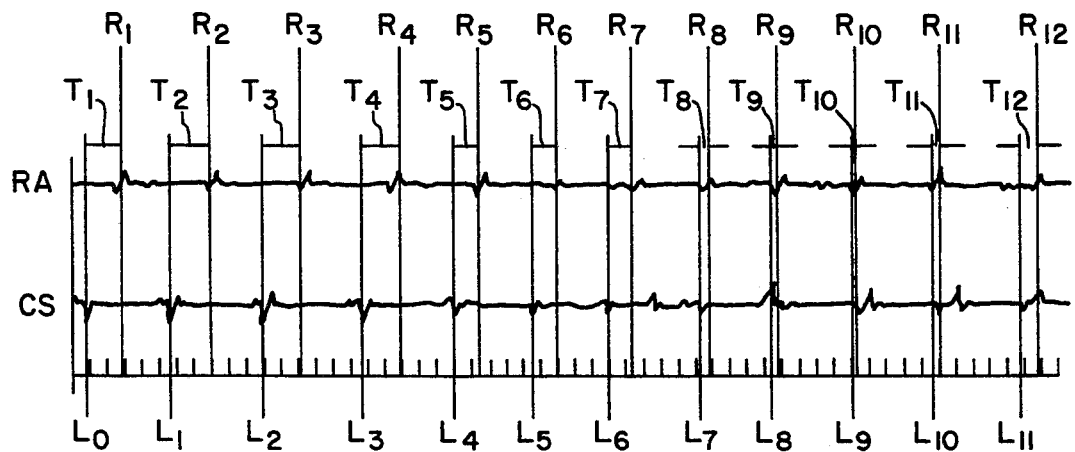
FIG. 3 is an electrogram illustrating fibrillation as indicated by two electrodes connected to the heart.
Figure 4:
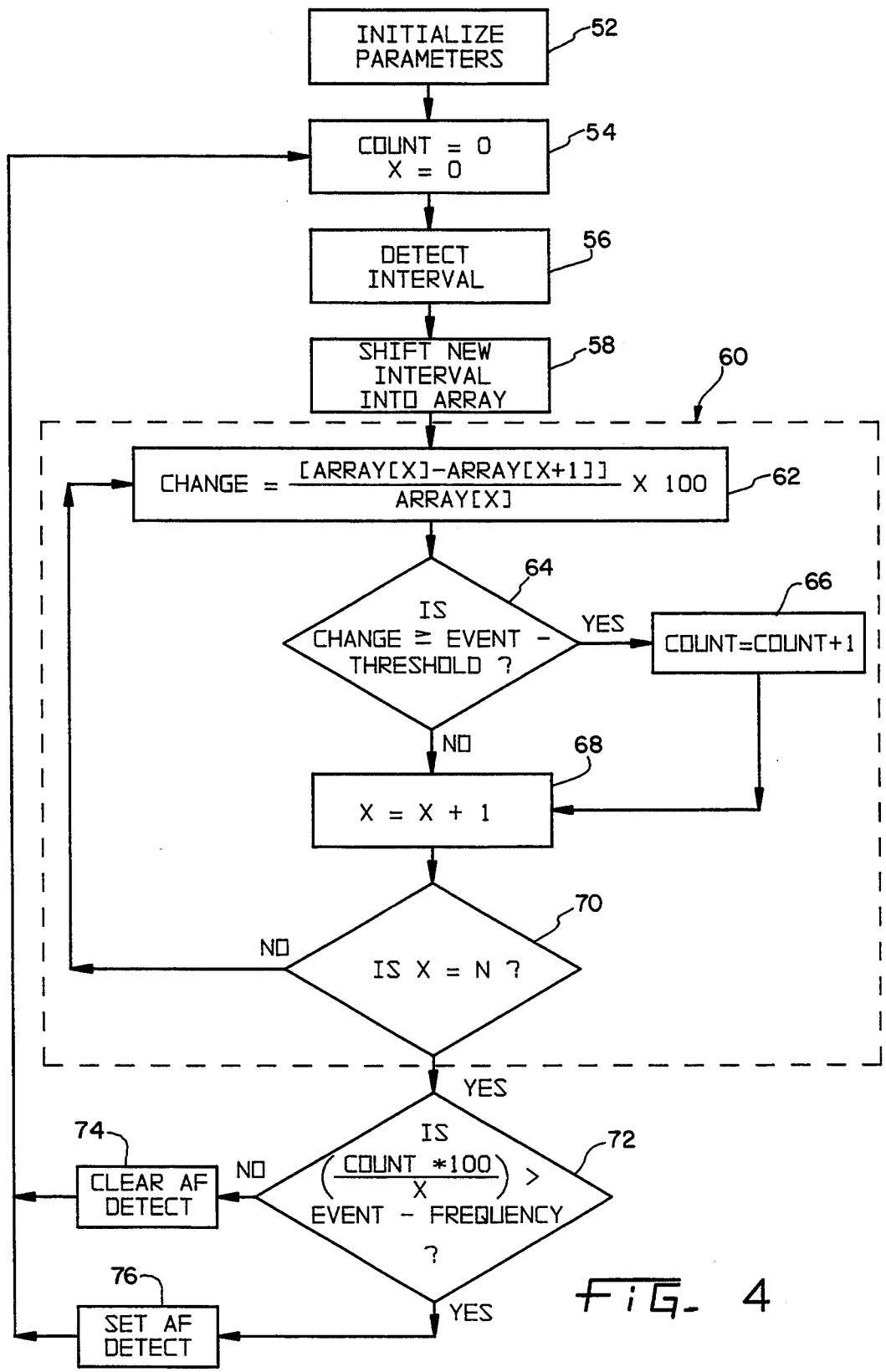
FIG. 4 is a flow chart diagram of the fibrillation detection method of the present invention.

The present invention is an apparatus and method for detecting fibrillation in the heart and delivering appropriate defibrillating shocks. FIG. 1 shows a schematic diagram of the apparatus which monitors the electrical activity of the heart as the heart is activated, and delivers defibrillating shocks when fibrillation is detected. The electrodes connected to the apparatus of FIG. 1 are shown in contact with the left and right atrium of a heart in the drawing of FIG. 2. The electrical activity sensed over the electrodes are shown in FIG. 3 for both normal activations and fibrillation activations, with the enlarged view of FIG. 5 more particularly showing the detection of heart activation. FIG. 4 provides a flow chart representation of the process of fibrillation detection in one embodiment of the present invention, with the process of defibrillation being represented in the flow chart of FIG. 6.

FIG. 1 shows a schematic diagram of fibrillation detector and defibrillator 10 which includes sensing portion 12, analyzing portion 14, shock delivering portion 16, and programming portion 18. Sensing portion 12 includes electrogram amplifiers 20 and 22 which are coupled to electrogram detectors 24 and 26, respectively. The circuitry of sensing portion 12 may include discrete components, or alternatively, an analog ASIC chip. Analyzing portion 14 is connected to electrogram detectors 24 and 26 as start and stop inputs, respectively, to interval (delta activation or "ΔT") calculator 28. Interval calculator 28 is then connected to delta activation interval storage 30, which stores an array of delta activation interval values, with the number of delta activation interval values being indicated by programming portion 18. The circuitry of analyzing portion 14 and programming portion 18 includes storage circuitry which may include a microprocessor and associated memory, or alternatively an ASIC. The delta activation interval array is input as data for interval compare 32 which compares each delta activation interval value with the previous delta activation interval value to determine if fibrillation is evident according to a percentage indicated by programming portion 18. The result of the comparison is output to atrial fibrillation detect 34 as either an event or a non-event, and fibrillation detect 34 then determines if the accumulated record of events and non-events evidences a fibrillation condition, based on either an absolute number of events or a percentage of events according to the number or percentage indicated by programming portion 18. If a fibrillation condition is evidenced, then fibrillation detect 34 sets a flag that signals the presence of the fibrillation condition to defibrillator 16 which may then, if appropriate, deliver defibrillating shocks to the heart.

The term "event" as used in this application refers to an observed condition of the heart rhythm which may indicate an irregular condition. An irregular condition is a change in the time interval between regional activations in the left and right sides of the heart. For example, if the time interval between the n-th heart activation and the (n+1)-th activation exceeds an expected or baseline time by a certain percentage, then that time interval is considered an "event". Although the occurrence of a single event is not determinative of the presence of an arrhythmic condition, the present invention monitors the frequency of events to determine whether a fibrillation condition should be indicated. The exact parameters which are used to detect events and to evaluate whether fibrillation should be indicated are stored in programming portion 18.

The values specified in programming portion 18 are to be determined by the physician treating the patient employing defibrillator 10. The values relating to sensitivity and refractory period are for tuning sensing portion 12 to the particular heart rhythms of the patient, as is well known. However, the values relating to the number of intervals and events, the threshold deviation percentage, and the event frequency percentage must be set to provide the desired detection performance as described in more detail below.

Figure 2:
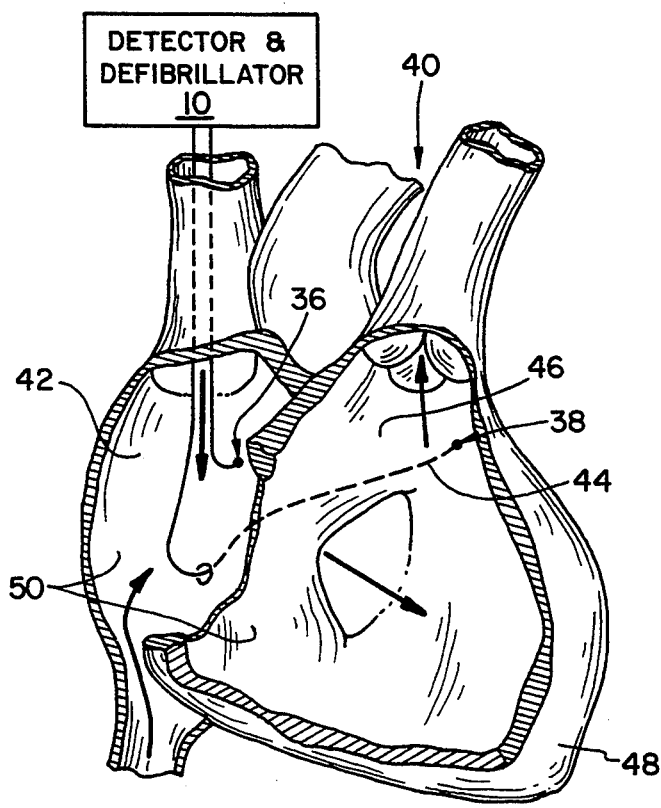
FIG. 2 is a drawing of a heart, in partial cut-away, showing the connection of the electrodes to the heart.

FIG. 2 shows defibrillator 10 connected with right atrial electrode 36 and left atrial electrode 38, both of which are located in heart 40. Specifically, right atrial electrode 36 is located close to right atrium 42, preferably in the high right atrium, or may alternatively be placed epicardially on right atrium 42; left atrial electrode 38 is located close to left atrium 46 preferably in proximal or distal coronary sinus 44, or alternatively be placed epicardially on left atrium 46. Electrodes 36 and 38 may be suitably implanted recording leads, unipolar or bipolar, as is well known; electrodes 36 and 38 are structured and arranged to monitor local electrical signals in the body tissue. The correct placement of the electrodes helps to minimize the amount of noise present on the electrodes. Further, in order to detect ventricular fibrillation, electrodes 36 and 38 may be located in the left and right ventricles 48 and 50, respectively. In fact, the present invention may be applied to any two anatomically distinct atrial or ventricular sites. However, for the purposes of explanation in this application, only atrial fibrillation is discussed below.

Figure 5:
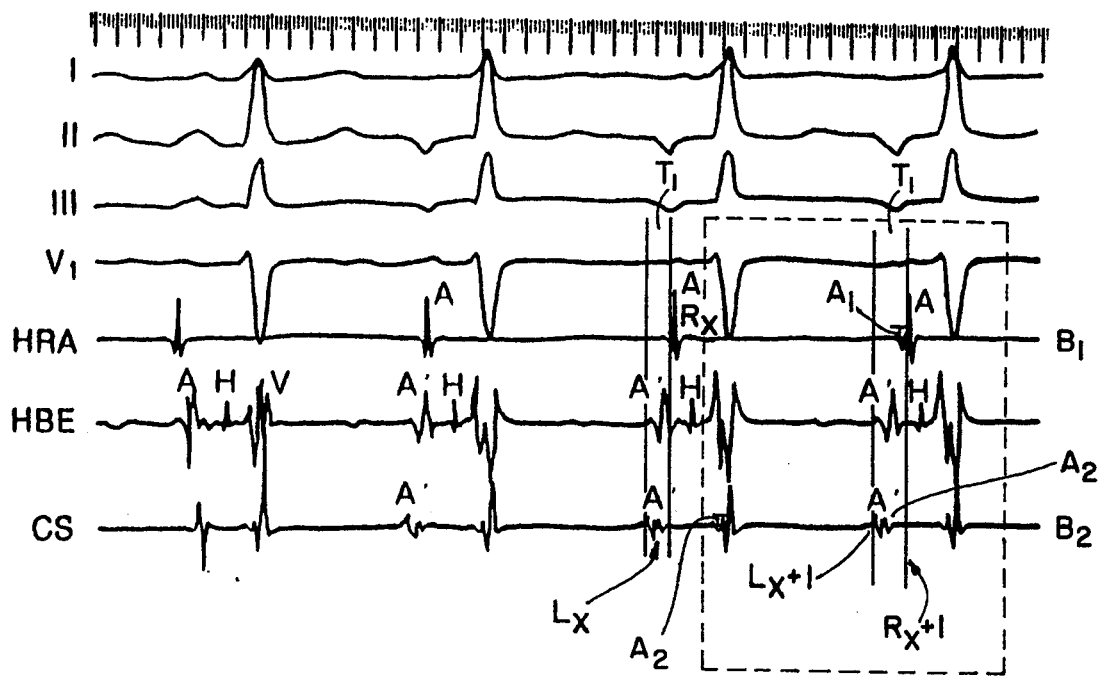
FIG. 5 is an electrogram showing the detection of localized heart activations.

FIG. 5 shows an electrogram of regional electrical activations, or pulses, detected at the two atrial sites shown in FIG. 2. Electrical activity detected by electrode 36, implanted in right atrium 42, is indicated by the HRA signal line which is received by sensing portion 12. Similarly, electrical activity detected by electrode 38, implanted in the coronary sinus 44, is indicated by the CS signal line which is received by sensing portion 12. Also included in FIG. 5 are signal lines for the low right atrium (HBE) and other leads of an ECG (I-III and $V_1$). The location of the electrodes in the heart facilitates sensing activations accurately, as the HBE and other leads cannot be monitored as accurately in the detection method described below. Preferably, electrodes 36 and 38 record electrical activity from a relatively circumscribed area, for example, within an area of 0.5 mm to several centimeters in diameter. In fact, a single electrode could be used as long as the single electrode could distinguish between two different localized signals and thereby provide electrograms for the left and right sides of the heart.

The values for sensitivity and refractory period determine when sensing portion 12 detects an activation in either the left atrium, indicated by $L_x$ and $L_{x+1}$ on the CS signal, or the right atrium, indicated by $R_x$ on the HRA signal.

The sensitivity value for tuning sensing portion 12 relates to the threshold of electrocardiographic activity which is required in order for sensing portion 12 to detect a signal in a conventional manner. The sensitivity value specifies the level, an absolute value of deviation (labeled "$A_1$" and "$A_2$" on FIG. 5) from the baseline (labeled "$B_1$" and "$B_2$" on FIG. 5) of the localized electrocardiographic activity. Sensitivity values are specific for each patient's and are conventionally determined by monitoring the patient's electrocardiographic signals. For example, a sensitivity level may initially be set to twenty percent (20%) of the maximum detected signal, then modified depending on the consistency of sensing localized heart activations. If the sensitivity value is too high, atrial activation irregularities may be missed. If this value is too low, signal noise from other parts of the heart may falsely indicate an atrial activation. Accordingly, each patient has a particular sensitivity level which is empirically determined.

The refractory period specifies the amount of time sensing is deactivated by sensing portion 12 after a threshold occurs, previous to monitoring the electrical activity for the completion of an activation. Each activation includes a number of instances when the absolute value of the localized electrical signal exceeds the sensitivity level, and then the activation is followed by a significantly longer amount of time in which the localized electrical signal remains around the baseline. The refractory period sets an amount of time in which the localized electrical signal is disregarded before again checking for it exceeding the sensitivity level. For example, a refractory period of 100 ms may be sufficient to accurately detect activations, and would only fail to detect an activation if the heart rate was over 600 beats per minute. However, if ventricular electrical signals, which occur fairly concomitantly with atrial electrical signals, cause false indications of activations, the refractory period may be increased to eliminate such false indications. As with sensitivity values, each patient uses a particular refractory period which is empirically determined.

Therefore, when the CS signal goes above the sensitivity value associated with the left atrium, the first left atrial activation $L_x$ is detected. The CS signal is then disregarded for the refractory period, after which the CS signal should return to the baseline. At the same time, the HRA signal is monitored to determine when it exceeds the sensitivity value associated with the right atrium. When exceeded, the first right atrial activation $R_x$ is detected and the RA signal is then disregarded for the refractory period. This interval between $L_x$ and $R_x$, $T_1$, may be measured and recorded by starting and stopping a timer. Subsequently, the CS signal is monitored for exceeding its sensitivity level so that the second left atrial activation $L_{x+1}$ is detected, indicating the completion of a cycle.

With the sensitivity values and refractory period values appropriately set, the time intervals between left and right atrial activations may be measured and compared. FIG. 3 shows a graph of electrical activations from right atrium 42 (labeled as signal line RA and activation points $R_i$) and electrical activations from left atrium 46 (labeled as signal line CS for coronary sinus and activation points $L_i$). Normally, activations from the left ($L_i$) and right ($R_i$) atrium are regularly spaced apart in time, e.g., every 0.1 second after an activation occurs in one atrium, an activation from the other atrium occurs. This is exemplified by the intervals $T_1$–$T_4$ of FIG. 3. However, when fibrillation occurs, then the timing of activations from the left and right atrium are not related. This is exemplified by intervals $T_5$–$T_{12}$ of FIG. 3. Thus, to detect fibrillation, the time interval between activations from the left and right atrium is calculated and compared to previous intervals. The previous intervals may be the last n discrete number of activations, although alternatively a normalized activation interval may be determined over a test period for a particular patient, so that a base line characteristic may be established and stored in program portion 18. If the calculated time interval deviates substantially from the previous time intervals, either by an absolute amount, by a percentage, or by any other irregular rhythms, then the existence of fibrillation may be confirmed. Both the rhythm, repetitive nature, and rate of the atrial activations are unrelated to each other during fibrillation, whereas in all other identified tachyarrhythmias, electrical activity in the atria is harmonious.

The method of fibrillation detection, in one embodiment, is illustrated in the flow chart of FIG. 4. First, the parameters must be set in the initialization step 52. This may involve hard-wiring dedicated circuitry with the desired sensitivity and refractory period values for left and right, storing those values in Programmable Read Only Memory (PROM), Erasable PROM (EPROM), or Electrically Erasable PROM (EEPROM), or alternatively having a microprocessor based system wherein the values are stored in Random Access Memory (RAM). Also, the values involving the threshold percentages and frequencies may be stored in similar circuitry in programming portion 18.

Further, an array of N+1 data pairs is stored for the last N+1 cycles. Each data pair includes both cycle length and the interval between left and right activations, and the stored data pairs allow for calculation of percentage change between the N cycles. The array may be initially loaded with normalized values so that erroneous detection is avoided when initially observing activations from the sensors.

After initialization step 52, the first step of detection loop involves setting the event counter ("count") and the loop counter ("x") both to 0 in step 54. Next, detect interval step 56 involves monitoring electrodes 36 and 38 to determine that a cycle has occurred ($R_i$ to $R_{i+1}$) and that an interval has been measured ($R_i$ to $L_i$). If a cycle is detected but no $L_i$ activation has been observed, and hence no interval is measured, then a separate no-interval counter is incremented. Usually, a large value for the no-interval counter indicates that the sensitivity and refractory period values are not properly adjusted.

Once a new pair of cycle and interval values are determined in step 56, that new value pair is shifted into the array in step 58, with the oldest value pair being shifted out and discarded. Thus, the array is ready for processing in loop portion 60 of the flow chart. The first step of loop portion 60 involves calculating the percentage change in the interval value in step 62. The calculation is made according to the equation:

$$\text{Percentage Change} = \frac{|\text{array}[x] - \text{array}[x-1]|}{\text{array}[x]} * 100$$

where x represents the index into the array, so that the absolute difference between the specified interval and its previous interval is divided by the specified interval and multiplied by one hundred to arrive at the percentage. Next in step 64, the percentage change is compared to the event-threshold percentage stored in programming portion 18. If the percentage change is greater than the event-threshold, then the variable "count" is incremented by one in step 66. In either case, "x" is incremented by one in step 68 before comparing x to N in step 70. If not equal, loop portion 60 continues by returning to step 62. If equal, then fibrillation is checked for in step 72 by comparing the observed event percentage, calculated as the value of "count" divided by "x" (or N) and then multiplied by 100, with the event-frequency value stored in programming portion 18. If the observed event percentage is greater than the event-frequency value, step 74 clears the atrial fibrillation (AF) detect signal, otherwise step 76 sets the AF detect signal. Then the process is repeated by returning to step 54 to add another interval value pair and re-evaluate the observed event percentage.

Figure 6:
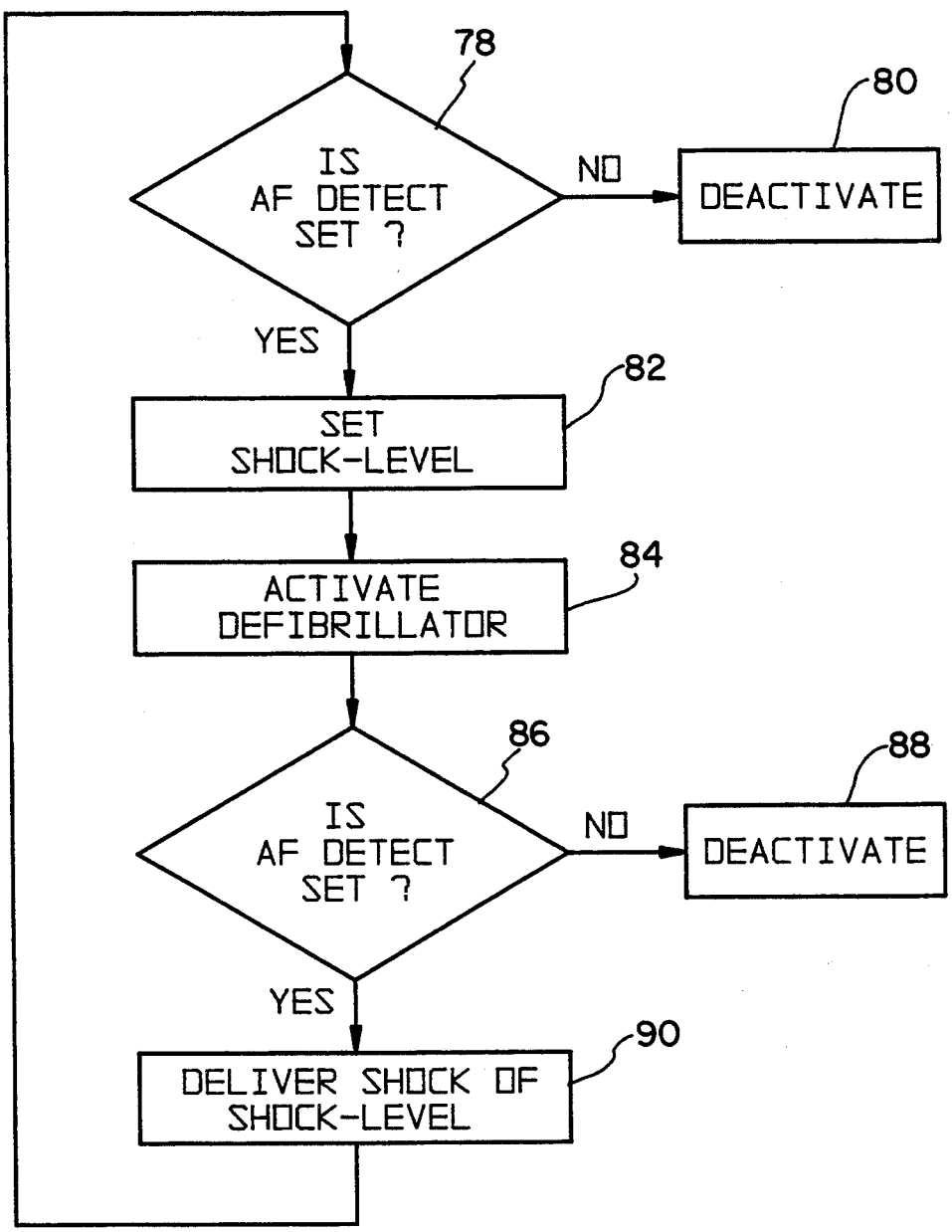
FIG. 6 is a flow chart diagram of the defibrillation method of the present invention.

The present invention also contemplates the delivery of defibrillating shocks by defibrillator 16, as represented by the flow chart of FIG. 6. Periodically, defibrillator 16 checks the AF Detect flag in step 78, and if no atrial fibrillation is detected, then defibrillator 16 is deactivated in step 80. Once the AF Detect flag is set, the Shock-Level is set to a predetermined level in step 82 and the shock inducing portions of defibrillator 16 are activated in step 84. In step 82, the initial Shock-Level is set, which may be programmable, for example 0.1 joule. In subsequent iterations of step 82, additional higher Shock-Levels may be set which may also be programmable, for example in 0.1 joule increments or by values stored in a look-up table. After the appropriate Shock-Level is set in step 82 and defibrillator 16 is activated in step 84, the AF detect flag is again checked in step 86, and if no longer set then defibrillator 16 is deactivated in step 88. Otherwise, defibrillator 16 provides a defibrillation shock at the level specified by the variable Shock-Level in step 90, which discharges and deenergizes the defibrillation circuitry. The success of the defibrillation attempt is checked by repeating step 78. If the first defibrillating shock does not arrest the fibrillation, the next level of defibrillating shock, e.g. a 0.1 joule increase over the previous level, is then set and the defibrillator is re-activated for delivering another shock. This process is repeated until the fibrillation condition is no longer detected.

The defibrillating shocks delivered to the atria generally do not exceed 2 joules, and rarely approach 10 joules. However, if the power level of the defibrillation shocks to the atria approaches a sufficiently high level that it may influence the ventricles, then the defibrillation shock is to be delivered at a precise time in relation to the ventricular heart beat. This may be done by monitoring the ventricular rhythm, or by using a pacemaker to establish the basic ventricular rhythm and synchronizing the defibrillation shocks to the ventricular rhythm. Also, if the present invention is used on the ventricles, where a greater defibrillating shock is necessary, then the programmable amounts of defibrillating shock may range from as low as 0.1 joules to as high as 30 or 40 joules.

In the exemplary embodiment, the electrodes implanted in the right atrium and coronary sinus are conventional heart implants for monitoring, pacing, and defibrillating which have a closely spaced pair of electrodes for localized electrical measurement, with the electrodes being spaced apart by about 1 or 2 mm. The electrodes are connected to an isolated differential preamplifier (preamp), with a gain of about 1000 and a frequency response in the range of 30–500 Hz. The preamp is connected to an analog-to-digital conversion board, specifically a National Instruments NB-MIO-16XH set, configured for single-ended bipolar, $\pm 10$ Volt inputs, and a corresponding interface block. The analog-to-digital conversion board is installed in a Macintosh IIfx computer preferably having at least 8 megabytes of random access memory (RAM). The fibrillation detection method is implemented in software using the Macintosh computer running under the System 7.0 operating system, specifically using the LabVIEW 2.2 instrumentation software from National Instruments. However, one skilled in the art understands that such implementation may be made in hardware (an ASIC chip) or with other software (operating on a general purpose microprocessor with associated memory).

Although atrial defibrillators are not yet commercially available, a programmable ventricular defibrillator may be adapted to operate according to the present invention. For example, the Pacer Cardioverter Defibrillator (model number 7217B) made by Medtronic of Minneapolis, Minn., is such a device which is adaptable to operate according to the present invention. The Pacer Cardioverter Defibrillator may be modified to be coupled to atrial electrodes, monitor those electrodes according to the present invention, and deliver defibrillating shocks to the atrium which are significantly less intensive than shocks conventionally administered for ventricular fibrillation.

The disclosure above specifies the location of the electrodes in particular areas of the heart. As is well known in the medical field, such electrodes may be located epicardially, endocardially, or intramurally. For epicardially locating the electrodes on the atrium, one electrode may be located on the right atrial appendage and the other in the left atrial appendage. For endocardially locating the electrodes in the atrium, one electrode may be located in the proximal or distal coronary sinus (adjacent to the left atrium) and the other in the right atrial appendage. Further, although an atrial arrangement is shown in the Figures, the present invention may also be used on the ventricular portions of the heart. For epicardially locating the electrodes on the ventricles, one electrode may be located on the outside of the right ventricle and the other on the outside of the left ventricle. For endocardially locating the electrodes in the ventricles, one electrode may be located in the apex of the right ventricle and the other electrode in the outflow track of the right ventricle.

While this invention has been described as having a preferred design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method of detecting fibrillation comprising the steps of:
   locating two electrodes at two different positions in the heart, one electrode in the right atrium to monitor local electrical signals, and locating the other electrode in the coronary sinus proximal to the left atrium to monitor local electrical signals;
   monitoring said electrical signals detected by the two electrodes to determine the occurrence of an activation;
   measuring the time interval between said activations; and
   comparing the measured time interval with a reference time interval value and calculating whether the measured time interval substantially deviates from the reference time interval value to thereby ascertain the presence of fibrillation.

2. The method of claim 1 wherein said reference time interval value is a stored value of a previously determined time interval.

3. The method of claim 1 further comprising the step of storing a plurality of said measured time interval values, and said comparing step includes determining the frequency of deviation from said reference time interval value.

4. The method of claim 3 further comprising the step of comparing said frequency of deviation with a predetermined frequency to ascertain the presence of a fibrillation condition.

5. The method of claim 1 further comprising the step of storing a plurality of said measured time interval values, and said comparing step includes comparing each of said plurality of measured time interval values with the preceding one of said plurality of measured time interval values, said comparing step also includes determining how many of said plurality of measured time interval values substantially deviate from the preceding said measured time interval to determine the frequency of deviation, and said comparing step further includes comparing said frequency of deviation with a reference frequency to ascertain the presence of a fibrillation condition.

6. The method of claim 1 further comprising the step of sensing cycles on one of the electrodes, and the step of determining if an activation was sensed by the other electrode during each said cycle.

7. The method of claim 6 further comprising the step of recording each said cycle in which no activation was sensed by the other electrode.

8. The method of claim 1 wherein said monitoring step includes determining when the absolute value of the electrical signal exceeds a sensitivity level to indicate an activation.

9. The method of claim 8 wherein after an activation is indicated, said monitoring step further includes disregarding the electrical signal for a refractory period before again monitoring the electrical signals.

10. A method of detecting fibrillation comprising the steps of:
    locating two electrodes at two different positions in the atrium, each electrode being adapted to sense electrical signals;
    monitoring said electrical signals detected by the two electrodes to determine the occurrence of an activation;
    measuring the time interval between said activations;
    comparing the measured time interval with a reference time interval value and calculating whether the measured time interval substantially deviates from the reference time interval value;
    determining the presence of fibrillation based upon whether a substantial deviation is calculated in comparing step.

11. A method of detecting and treating fibrillation comprising the steps of:
    locating two electrodes at two different positions in the atrium, each electrode being adapted to sense electrical signals;
    monitoring said electrical signals detected by the two electrodes to determine the occurrence of an activation;
    measuring the time interval between said activations;
    comparing the measured time interval with a reference time interval value and calculating whether the measured time interval substantially deviates from the reference time interval value to thereby ascertain the presence of fibrillation; and
    if fibrillation is indicated, delivering defibrillation shocks to the heart with the electrodes.

12. The method of claim 11 wherein said reference time interval value is a stored value of a previously determined time interval.

13. The method of claim 11 further comprising the step of storing a plurality of said measured time interval values, and said comparing step includes determining the frequency of deviation from said reference time interval value.

14. The method of claim 13 further comprising the step of comparing said frequency of deviation with a predetermined frequency to ascertain the presence of a fibrillation condition.

15. The method of claim 11 further comprising the step of storing a plurality of said measured time interval values, and said comparing step includes comparing each of said plurality of measured time interval values with the preceding one of said plurality of measured time interval values, said comparing step also includes determining how many of said plurality of measured time interval values substantially deviate from the preceding said measured time interval to determine the frequency of deviation, and said comparing step further includes comparing said frequency of deviation with a reference frequency to ascertain the presence of a fibrillation condition.

16. The method of claim 11 further comprising the step of sensing cycles on one of the electrodes, and the step of determining if an activation was sensed by the other electrode during each said cycle.

17. The method of claim 16 further comprising the step of recording each said cycle in which no activation was sensed by the other electrode.

18. The method of claim 11 wherein said step of delivering defibrillation shocks comprises the steps of:
   delivering a relatively low level defibrillation shock;
   checking for the continued presence of fibrillation;
   if fibrillation continues to exist then increasing the level of defibrillation shock, delivering the increased defibrillation shock, and checking for the continued presence of fibrillation until no fibrillation is apparent.

19. The method of claim 11 wherein said locating step includes locating one electrode in the right atrium to monitor local electrical signals and locating the other electrode in the coronary sinus proximate to the left atrium to monitor local electrical signals.

20. The method of claim 11 wherein said monitoring step includes determining when the absolute value of the electrical signal exceeds a sensitivity level to indicate an activation.

21. The method of claim 20 wherein after an activation is indicated, said monitoring step further includes disregarding the electrical signal for a refractory period before again monitoring the electrical signals.

22. An apparatus for detecting arrhythmia, the apparatus adapted for use on a heart, said apparatus comprising:
   first and second electrodes adapted to contact the heart and sense electrical signals from the heart, said electrodes being disposed at two different locations;
   means for monitoring said electrical signals detected by said first and second electrodes to determine the occurrence of an activation, said monitoring means including means for measuring the time interval between said activations, said monitoring means further including means for disregarding the electrical signal after an activation is indicated for a refractory period before again monitoring the electrical signal; and
   means for comparing the measured time interval with a reference time interval value and calculating whether the measured time interval substantially deviates from the reference time interval value, said comparing means including means for indicating the presence of a fibrillation condition in the heart.

23. The apparatus of claim 22 further comprising means for storing a measured time interval value as said reference time interval value.

24. The apparatus of claim 22 further comprising means for storing a plurality of measured time values, and said comparing means includes means for determining the frequency of deviation from said reference time interval value.

25. The apparatus of claim 24 wherein said comparing means includes means for comparing said frequency of deviation with a reference frequency to ascertain the presence of fibrillation.

26. The apparatus of claim 22 further comprising means for storing a plurality of measured time interval values, said comparing means includes means for comparing each of said plurality of measured time interval values with the preceding one of said plurality of measured time interval values, said comparing means also includes means for determining how many of said plurality of measured time interval values substantially deviate from the preceding said measured time interval value to determine the frequency of deviation, and said comparing means further includes means for comparing the frequency of deviation with a reference frequency to ascertain the presence of a fibrillation condition.

27. The apparatus of claim 22 further comprising means for sensing cycles on said first electrode and means for determining if an activation was sensed by said second electrode during each said cycle.

28. The apparatus of claim 27 further comprising means for recording each said cycle in which no activation was sensed by said second electrode.

29. The apparatus of claim 22 wherein said electrodes have a size and shape capable of being disposed in the atrium.

30. The apparatus of claim 22 wherein said first electrode has a size and shape capable of being disposed in the right atrium and has means for detecting local electrical signals, and said second electrode has a size and shape capable of being disposed in the coronary sinus proximate to the left atrium and has means for detecting local electrical signals.

31. The apparatus of claim 22 wherein said monitoring means determines when the absolute value of the electrical signal exceeds a sensitivity level to determine the occurrence of an activation.

32. The apparatus of claim 22 wherein said apparatus has a size and shape capable of being implanted in the human body.

33. An apparatus for detecting and treating arrhythmia, the apparatus adapted for use on a heart, said apparatus comprising:
   first and second electrodes adapted to contact the heart and sense electrical signals from the heart, said electrodes being disposed at two different locations;
   means for monitoring said electrical signals detected by said first and second electrodes to determine the occurrence of an activation, said monitoring means including means for measuring the time interval between said electrical activations, said monitoring means further including means for disregarding the electrical signal after an activation is indicated for a refractory period before again monitoring the electrical signal;
   means for comparing the measured time interval with a reference time interval value and calculating whether the measured time interval substantially deviates from the reference time interval value, said comparing means including means for indicating the presence of a fibrillation condition in the heart; and
   means for delivering defibrillating shocks to the heart, said defibrillating means being responsive to said indicating means.

34. The apparatus of claim 33 further comprising means for storing a measured time interval value as said reference time interval value.

35. The apparatus of claim 33 further comprising means for storing a plurality of measured time values, and said comparing means includes means for determining the frequency of deviation from said reference time interval value.

36. The apparatus of claim 35 wherein said comparing means includes means for comparing said frequency of deviation with a reference frequency to ascertain the presence of fibrillation.

37. The apparatus of claim 33 further comprising means for storing a plurality of measured time interval values, said comparing means includes means for comparing each of said plurality of measured time interval values with the preceding one of said plurality of measured time interval values, said comparing means also includes means for determining how many of said plurality of measured time interval values substantially deviate from the preceding said measured time interval value to determine the frequency of deviation, and said comparing means further includes means for comparing the frequency of deviation with a reference frequency to ascertain the presence of a fibrillation condition.

38. The apparatus of claim 33 further comprising means for sensing cycles on said first electrode and means for determining if an activation was sensed by said second electrode during each said cycle.

39. The apparatus of claim 38 further comprising means for recording each said cycle in which no activation was sensed by said second electrode.

40. The apparatus of claim 33 wherein said delivering means is coupled to at least one of said first and second electrodes for delivering said defibrillating shocks.

41. The apparatus of claim 33 wherein said delivering means includes means for applying a low level defibrillating shock, means for checking for the continued presence of the fibrillation condition, and means for increasing the level of said defibrillating shock and applying said defibrillating shock until no fibrillation is apparent.

42. The apparatus of claim 41 wherein said applying means initially provides a defibrillating shock of about 0.1 joules, and said increasing means increases the level of said defibrillating shock by about 0.1 joules.

43. The apparatus of claim 33 wherein said electrodes have a size and shape capable of being disposed in the atrium.

44. The apparatus of claim 33 wherein said first electrode has a size and shape capable of being disposed in the right atrium and has means for detecting local electrical signals, and said second electrode has a size and shape capable of being disposed in the coronary sinus proximate to the left atrium and has means for detecting local electrical signals.

45. The apparatus of claim 33 wherein said monitoring means determines when the absolute value of the electrical signal exceeds a sensitivity level to determine the occurrence of an activation.

46. The apparatus of claim 33 wherein said apparatus has a size and shape capable of being implanted in the human body.

47. A method of detecting fibrillation comprising the steps of:
locating two electrodes at two different positions in the heart, each electrode being adapted to sense electrical signals;
monitoring said electrical signals detected by the two electrodes to determine the occurrence of an activation, and after an activation is indicated, said monitoring step further including disregarding the electrical signal for a refractory period before again monitoring the electrical signals;
measuring the time interval between said activations; and
comparing the measured time interval with a reference time interval value and calculating whether the measured time interval substantially deviates from the reference time interval value to thereby ascertain the presence of fibrillation.

48. A method of detecting and treating fibrillation comprising the steps of:
locating two electrodes at two different positions in the heart, each electrode being adapted to sense electrical signals;
monitoring said electrical signals detected by the two electrodes to determine the occurrence of an activation, and after an activation is indicated, said monitoring step further including disregarding the electrical signal for a refractory period before again monitoring the electrical signals;
measuring the time interval between said activations;
comparing the measured time interval with a reference time interval value and calculating whether the measured time interval substantially deviates from the reference time interval value to thereby ascertain the presence of fibrillation; and
if fibrillation is indicated, delivering defibrillation shocks to the heart with the electrodes.

49. An apparatus for use in detecting fibrillation in the atrium, said apparatus comprising:
first and second electrodes capable of being disposed at different locations in the atrium, each of said first and second electrodes having means for detecting local electrical signals in the atrium;
means for monitoring said electrical signals detected by said first and second electrodes to determine the occurrence of an activation, said monitoring means including means for measuring the time interval between said activations; and
means for comparing the measured time interval with a reference time interval value and calculating whether the measured time interval substantially deviates from the reference time interval value, said comparing means including means for indicating the presence of a fibrillation condition in the heart.

50. An apparatus for use in detecting and treating fibrillation in the atrium, said apparatus comprising:
first and second electrodes capable of being disposed at different locations in the atrium, each of said first and second electrodes having means for detecting local electrical signals in the atrium;
means for monitoring said electrical signals detected by said first and second electrodes to determine the occurrence of an activation, said monitoring means including means for measuring the time interval between said electrical activations;
means for comparing the measured time interval with a reference time interval value and calculating whether the measured time interval substantially deviates from the reference time interval value, said comparing means including means for indicating the presence of a fibrillation condition in the heart; and
means for delivering defibrillating shocks to the heart, said defibrillating means being responsive to said indicating means.

* * * * *

UNITED STATES PATENT AND TRADEMARK OFFICE
CERTIFICATE OF CORRECTION

PATENT NO. : 5,366,486
DATED : November 22, 1994
INVENTOR(S) : Douglas P. Zipes et al It is certified that error appears in the above-indentified patent and that said Letters Patent is hereby corrected as shown below:

On the title page, item [75]:

Inventors" delete "Doulgas" and insert therefor --DOUGLAS--.

Signed and Sealed this

Seventh Day of March, 1995

Attest:

BRUCE LEHMAN

*Attesting Officer*     *Commissioner of Patents and Trademarks*